(12) United States Patent
Domb et al.

(10) Patent No.: US 7,943,169 B2
(45) Date of Patent: May 17, 2011

(54) ABSORBABLE SOLID COMPOSITIONS FOR TOPICAL TREATMENT OF ORAL MUCOSAL DISORDERS

(75) Inventors: Avraham J. Domb, Erfat (IL); Joseph Simcha Wolnerman, Jerusalem (IL)

(73) Assignee: Axiomedic Ltd, Gibralter (GI)

( * ) Notice: Subject to any disclaimer, the term of this patent is extended or adjusted under 35 U.S.C. 154(b) by 1319 days.

(21) Appl. No.: 10/083,413

(22) Filed: Feb. 27, 2002

(65) Prior Publication Data

US 2003/0003140 A1    Jan. 2, 2003

Related U.S. Application Data

(60) Provisional application No. 60/271,735, filed on Feb. 28, 2001.

(51) Int. Cl.
| | |
|---|---|
| *A61K 9/20* | (2006.01) |
| *A61K 33/36* | (2006.01) |
| *A01N 65/00* | (2009.01) |
| *A01N 37/18* | (2006.01) |
| *A01N 43/04* | (2006.01) |
| *A01N 31/00* | (2006.01) |

(52) U.S. Cl. .................. 424/464; 424/667; 424/725
(58) Field of Classification Search .................. 424/449, 424/448, 434, 725, 49, 58; 514/909, 900, 514/54, 57
See application file for complete search history.

(56) References Cited

U.S. PATENT DOCUMENTS

| | | | |
|---|---|---|---|
| 4,226,848 A | * | 10/1980 | Nagai et al. |
| 4,276,287 A | * | 6/1981 | Carbardo, Jr. |
| 4,307,075 A | | 12/1981 | Martin |
| 4,772,470 A | * | 9/1988 | Inoue et al. |
| 5,456,745 A | * | 10/1995 | Roreger et al. ............ 106/140.1 |
| 5,719,197 A | * | 2/1998 | Kanios et al. |
| 5,939,050 A | * | 8/1999 | Iyer et al. |
| 5,942,244 A | * | 8/1999 | Friedman et al. |
| 6,159,498 A | * | 12/2000 | Tapolsky et al. |
| 6,197,305 B1 | * | 3/2001 | Friedman et al. |
| 6,207,137 B1 | * | 3/2001 | Shuch et al. |
| 6,303,147 B1 | * | 10/2001 | Gilis |
| 6,325,991 B1 | * | 12/2001 | Draheim |
| 6,458,777 B1 | * | 10/2002 | Sonis et al. |

FOREIGN PATENT DOCUMENTS

| | | |
|---|---|---|
| EP | 0 306 454 | 3/1989 |
| EP | 0 355 536 | 2/1990 |
| EP | 839524 A1 * | 10/1997 |
| EP | 000839524 A1 * | 5/1998 |
| WO | WO 97/24109 * | 7/1997 |
| WO | WO 00/18365 | 4/2000 |
| WO | WO 00/59423 | 10/2000 |

OTHER PUBLICATIONS

Lawless, Julia. The Illustratged Encyclopedia of Essential Oils: The Complete Guide to the Use of Oils in Aromatherapy and Herbalism. 1995. Element Books, USA, pp. 115, 120, 123, 134, 139-141 and 196-197.*

Lawless, Julia. The Illustrated Encyclopedia of Essential Oils: The Complete Guide to the Use of Oils in Aromatherapy and Herbalism. 1995. Element Books, USA, pp. 115, 120, 123, 134, 139-141 and 196-197.* http://www.quackwatch.com/01QuackeryRelatedTopics/homeo. html, "Homeopathy: The Ultimate Fake" by Dr. Stephan Barrett. Aug. 9, 1999.*

Green, J. G. The Herbal Medicine-Maker's Handbook: A Home Manual (2000). The Crossing Press, USA, pp. 275-285.*

* cited by examiner

*Primary Examiner* — Michele Flood
(74) *Attorney, Agent, or Firm* — Pabst Patent Group LLP

(57) ABSTRACT

The invention provides a solid, self-bioadhesive composition for topical application that adheres to the oral mucosal tissue comprising a therapeutically effective amount of at least one herbal or homeopathic active agent; and a pharmaceutically acceptable solid bioadhesive carrier in an amount from about 40 to 99 percent based on the weight of the whole composition.

27 Claims, No Drawings

ABSORBABLE SOLID COMPOSITIONS FOR TOPICAL TREATMENT OF ORAL MUCOSAL DISORDERS

This application claims benefit to Provisional Application No. 60/271,735 filed Feb. 28, 2001; the disclosure of which is incorporated herein by reference.

The present invention relates to oral care compositions in the form of a topical self-adhesive sticker that adheres to the oral tissue surface for treating mucosal disorders such as lesions, aphthous stomatitis, inflamation, microbial infection and toothache. The sticker is comprising at least a minimally effective amount of bioactive herb extract or essential oil. The herbal extract or essential oil is incorporated in the sticker as a powder prepared by evaporating plant extracts onto an inert carrier such as sugars, talc, silicone dioxide, titanium dioxide and other pharmaceutically acceptable inert powders. The bioactive powder is mixed with the adhesive carrier powder and compressed into tablet stickers. Of particular interest, this invention further relates to a method for treating oral mucosal lesions in humans by applying a topical adhesive sticker releasing a safe and effective amount of monoterpenes with three unsaturations to the oral cavity.

BACKGROUND OF THE INVENTION

Gingivitis, mucosal lesions, and periodontal disease, are all undesirable conditions that affect many people. It is generally believed that the primary cause is viral infection or immune response which leads to bacterial infection of anaerobic bacteria, especially gram-negative anaerobic bacteria, in the mouth.

Periodontal disease is an undesirable condition which has widespread occurrence. Periodontal disease is a major cause of tooth loss in adults. Periodontal disease affects the periodontum, which is the investing and supporting tissues surrounding a tooth (i.e., the periodontal ligament, the gingiva, and the alveolar bone). Gingivitis and periodontitis are inflammatory disorders of the gingiva and the deeper periodontal tissues, respectively. Gingivitis occurs from the dental plaque, and periodontitis is caused by the infection spreading to the periodontal pocket or space between the gingiva and the tooth root.

Microorganisms contribute to both the initiation and progression of gingivitis, plaque, and periodontal disease. Thus, in order to prevent or treat these conditions, these microorganisms must be suppressed by some means other than simple mechanical scrubbing. The invention relates to compositions and methods for the treatment of the viral diseases herpes labialis (cold sores or fever blisters), herpes genitalis, herpes zoster (shingles), varicella zoster (chickenpox); inflammatory diseases and/or diseases demonstrating compromise or reaction of the immune system including aphthous stomatitis (canker sores), oral mucositis (stomatitis) secondary to chemotherapy, allergic conjunctivitis, giant papillary conjunctivitis; and lesions of injury to the skin including photodermatitis (sunburn, specifically second degree sunburn), thermal burns and pressure sores (decubitus ulcers).

Recurrent herpes simplex stomatitis may occur on the lips or intraorally. Outbreaks may be associated with trauma, fatigue, menstrual cycle, emotional upset, or exposure to sunlight. Vesicles, or intraepithelial blisters, usually are preceded by burning, swelling and soreness in the area where lesions subsequently develop. Vesicles are small, 1 millimeter in diameter or less and may coalesce to form larger lesions. These vesicles rupture quickly leaving small ulcerations. The most common sites of recurrent intraoral lesions are the hard palate and attached gingiva. Lesions gradually heal within 7-10 days producing no scarring.

Herpes simplex 1 and/or herpes simplex 2 lesions can occur orally or genitally. Herpetic lesions usually develop within 4-7 days after contact and may vary in nature from non-specific itching and soreness to erythema on the skin or mucous membranes to the development of painful vesicles which erode and form superficial, circular ulcers with a red areola. The ulcers become crusted in a few days and usually heal in about 10 days, with scarring. Recurrent genital herpetic disease may be quite frequent and may be prolonged over many years.

Herpes zoster (shingles) lesions are characterized by vesicular eruption and neuralgic pain in the cutaneous areas supplied by peripheral sensory nerves in the dorsal root ganglia affected by the virus. Herpes zoster is usually activated by local lesions involving the nerve containing the latent virus, systemic disease, particularly Hodgkin's disease, or by suppression or compromise of the immune system. Following a prodromal period of 34 days including symptoms of chills, fever, malaise and G.I. disturbances, characteristic crops of vesicles on an erythematous base appear in cutaneous areas innervated by the affected root ganglia. The involved area of the skin is usually hyperesthetic and the associated pain may be severe. Lesions usually begin to dry and scab within 10-14 days, but the outbreak of new clusters of vesicles can prolong the disease episode for weeks. Post herpetic neuralgia associated with herpes zoster may persist for months or years. Herpes zoster is caused by the varicella-zoster virus, the same virus that causes chickenpox with chickenpox being the acute, invasive phase of the virus and zoster (shingles) being the reactivation of the latent phase.

The usual incubation period for chickenpox following exposure to the virus is 10-14 days and the lesions erupt in successive crops for up to 6 days. Lesions progress from macule to papule to vesicle and usually begin crusting within 6-8 hours. Itching associated with the lesions may be severe and it is important to prevent scratching which may lead to widespread infection and disfigurement.

Aphthous stomatitis lesions (canker sores) are characterized by the development of painful, recurring necrotizing ulcerations of the oral mucosa either as solitary or multiple lesions. Etiology is unclear; however, considerable evidence suggests the disease may be an immunologic hypersensitivity response to an L-form *streptococcus* bacterium. Precipitating factors in canker sore lesions may include trauma (dental procedures), self-inflicted bites (as in eating), endocrine changes (premenstrual periods, following childbirth, menopause), acute psychological problems (period of increased stress), and allergic responses (asthma, eating certain foods or taking certain medications).

The aphthous ulcer can begin as a single or a multiple superficial erosion of the oral mucosal epithelium covered by a gray membrane. The most common sites of occurrence are the mucosa of the lips and cheeks, soft palate, tongue, pharynx, and all locations of unattached (to bone) gingiva and mucosa. The ulcers persist for 7-10 days and heal gradually producing no scarring.

Oral mucositis (stomatitis), a common side effect of chemotherapy, may develop when chemotherapeutic agents used to treat various neoplastic diseases interfere with the maturation and replication of the cells that comprise the oral epithelium. The condition may be focal or generalized and involve the buccal mucosa, palate, tongue, floor of the mouth and the gingiva. Oral mucositis is painful and as a result patients neglect oral hygiene and fail to maintain adequate nutrition and hydration. The compromised epithelial barrier can also facilitate invasion of potentially lethal bacteria and fungi that may lead to local infections and/or septicemia.

Photodermatitis or sunburn results from overexposure of the skin to ultraviolet rays of 280-320 nm. Symptoms appear in 1-24 hours and peak in 72 hours. Changes in the epithelium of the skin range from mild erythema (first degree burn) to pain, swelling, skin tenderness and blisters (second degree burn). Fever, chills, weakness, dehydration and shock can occur if the sunburn is sufficiently severe and/or occupies a large portion of the body surface area. Upon eruption of any blisters formed or exfoliation, the skin may be hypervulnerable to infection and sunlight for up to several weeks.

Tissue injury caused by thermal burns results in protein denaturation, burn wound edema and loss of intravascular fluid volume due to increased vascular permeability. The depth of the burn may be described as first, second or third degree. Pain or sensitivity to the touch is usually associated with first and second degree burns and blister formation is a common presentation of second degree burns. The severity of the burn is judged by quantity of tissue (body surface area) involved. Pain, increased susceptibility to infection, and scarring are the most common complications associated with thermal burns.

A pressure sore (decubitus ulcer) results when tissues overlying a bony prominence have been subjected to prolonged pressure resulting in ischemic necrosis and ulceration. Decubitus ulcers can affect not only superficial tissues, but can also involve muscle and bone and the recognized stages of decubitus ulcer formation (Stage 1 through Stage 6) correspond to the tissue layers involved and the degree of involvement. The decubitus ulcer lesion, when open at any stage, poses a risk of infection and, dependent upon the depth of the lesion and the proper elimination of the pressure, can lead to tissue necrosis, epidermal desquamation, osteitis and septicemia. Surgical intervention may be required for deep lesions or lesions in which healing by current therapies is unsuccessful.

Allergic conjunctivitis may occur as part of a larger allergic syndrome, such as hayfever, or may occur alone as a result of direct contact with airborne substances such as pollen, fungus spores, various dusts, or animal danders. Itching and excessive lacrimation are prominent symptoms of allergic conjunctivitis as is edema and hyperemia of the conjunctiva. Release of endogenous histamine from mast cells seems largely responsible for the results of the allergic response.

Giant papillary conjunctivitis is a specific conjunctival inflammatory reaction to the materials used in the fabrication of soft contact lenses. Although the condition is similar to allergic conjunctivitis, it is characterized by papillary hypertrophy and probably represents a chronic conjunctival inflammatory reaction to denatured proteins that become adherent to the anterior lens surface. Conjunctival changes progress and include itching, lens instability, mucoid discharge and contact lens intolerance. Again, the release of endogenous histamine from mast cells seems largely responsible for the results of the allergic response.

There are a number of over-the-counter medications for cold sores (fever blisters), canker sores, oral ulcerations and the like, including Blistex, Zilacatin, and Campho Phenique. A prescription medication also is available, under the trademark Zovirax. However, for many persons suffering from cold sores, fever blisters, etc., none of these medications is very effective. Zovirax is effective when taken orally by interfering with the replication of the herpes virus at the genetic level. We are concerned that there is potential for adverse reactions any time a patient takes medication systemically that interferes with DNA replication because of the risk of the medication interfering with normal cell DNA replication within the body, as is known to occur as a result of chemotherapy agents which are targeted to interfere with genetic replication of cancer cells and sometimes produce long term adverse side effects.

There are no effective over-the-counter remedies or medications for the treatment of oral lesions related to herpes zoster (shingles), varicella zoster (chickenpox), photodermatitis (sunburn), thermal burns, pressure sores (decubitus ulcers), allergic conjunctivitis or giant papillary conjunctivitis that alter the progression or severity of any of these disease states. Analgesics, humectants, topical anesthetics, and antihistamines might provide temporary symptomatic relief in any or all of the above disease states, but will generally not change the course or severity of the disease or its lesions. Prescription medications are available for some of these disease indications. However, the only one which has proven any effectiveness in treatment is, again, oral (systemic) Zovirax which is used to treat herpes zoster and varicella zoster. Topical silver sulfadiazine 1% cream, also available by prescription, has been used to treat herpes zoster and pressure sores, but without de double-blind clinical trials showing effectiveness to support this therapy. Prescription topical debriding agents are available for the removal of the necrotic tissue associated with pressure sores; however, once the necrotic tissue has been removed, these agents must be discontinued as they will retard healing of the ulcer. Topical solutions are available, mostly by prescription, which contain vasoconstricting agents or steroids and act only to temporarily relieve the symptoms associated with conjunctivitis.

Conventional oral hygiene formulations are not effective in treating oral lesions as their main limitation is the contact time with the lesion surface and that the lesion is exposed to the oral environment.

Conventional oral formulations include toothpaste (including gels and gels for subgingival application), mouth rinses, mouth sprays, chewing gums, and lozenges (including breath mints). The choice of a carrier to be used is basically determined by the way the composition is to be introduced into the oral cavity. If a toothpaste (including tooth gels, etc.) is to be used, then a "toothpaste carrier" is chosen as disclosed in, e.g., U.S. Pat. No. 3,988,433, to Benedict, the disclosure of which is incorporated herein by reference (e.g., abrasive materials, sudsing agents, binders, humectants, flavoring and sweetening agents, etc.). If a mouth rinse is to be used, then a "mouth rinse carrier" is chosen, as disclosed in, e.g., U.S. Pat. No. 3,988,433 to Benedict (e.g., water, flavoring and sweetening agents, etc.). Similarly, if a mouth spray is to be used, then a "mouth spray carrier" is chosen or if a lozenge is to be used, then a "lozenge carrier" is chosen (e.g., a candy base), candy bases being disclosed in, e.g., U.S. Pat. No. 4,083,955, to Grabenstetter et al., which is incorporated herein by reference; if a chewing gum is to be used, then a "chewing gum carrier" is chosen, as disclosed in, e.g., U.S. Pat. No. 4,083,955, to Grabenstetter et al., which is incorporated herein by reference (e.g., gum base, flavoring and sweetening agents). The main limitation of these toothpaste, mouthwash, mouth rinse, gels, gums and lozenges formulations is the short contact time, typically for a few seconds, which is not enough for treating the lesion. In contrast to the present invention which focuses on the topical delivery of herbal agents to the infected site by placing a bioadhesive sticker loaded with herbal active agents onto the lesion or infected oral tissue which releases the active agents for at least 30 minutes.

Systemic delivery of drugs and peptides using the buccal rout of administration has been described in the literature. This route has been investigated clinically for the delivery of a substantial number of drugs. It is the traditional route for administration of nitroglycerin and is also used for buprenorphine and nifedipine. D. Harris & J. Robinson, 81 J. Pharmaceutical Sci. 1 (1992). The buccal mucosa is less permeable than the sublingual mucosa. The rapid absorption and high bioavailabilities seen with sublingual administration of drugs is not generally provided to the same extent by the buccal mucosa. D. Harris & J. Robinson, 81 J. Pharmaceutical Sci. 1, 2 (1992). The permeability of the oral mucosae is probably related to the physical characteristics of the tissues. The sublingual mucosa is thinner than the buccal mucosa, thus permeability is greater for the sublingual tissue. The palatal mucosa is intermediate in thickness, but is keratinized and thus less permeable, whereas the sublingual and buccal tissues are not keratinized.

The use of buccal delivery systems for systemic delivery of drugs have been reviewed by Shojaei (buccal mucosa as a rought for systemic drug delivery, a review, J. Pharm. Pharmaceut Sci. 1 (1), 15-30, 1998. A non-degradable device for the delivery of buprenorphine has been described (Guo, J. H., Drug Deliv. Ind. Pharmacy, 20, 2809-2821, 1994). The buccal delivery of lidocaine and prostaglandines has been reported by Nagai (J. Controll. Rel. 6, 353-360, 1987).

While buccal delivery systems have been suggested in prior art, the use of herbal and homeopatic medications for the treatment of oral mucosal lesions were not suggested. Dueto the safety risk of systemic uptake of drugs delivered by buccal delivery, the use of natural and safe herbal medication provide an attractive alternative for treating oral ulcers with high complience. The herbs mentioned in this invention are surprisingly effective in trating the various oral mucosal disorders.

There is an unmet need for an effective remedy for the viral diseases herpes labialis (cold sores or fever blisters), herpes genitalis, herpes zoster (shingles), varicella zoster (chickenpox); inflammatory diseases or diseases demonstrating compromise or reaction of the immune system such as aphthous stomatitis (canker sores), oral mucositis (stomatitis) secondary to chemotherapy, allergic conjunctivitis, giant papillary conjunctivitis; and lesions of injury, thermal burns and pressure sores.

SUMMARY OF THE INVENTION

It is an object of the present invention to provide a convenient herbal medication and treatment in the form of a long acting self-bioadhesive sticker to be placed onto oral mucosal lesions such as herpes labialis and aphthous stomatitis lesions, fever blisters, cold sores and canker sores, and the like.

It is an object of the present invention to provide a convenient herbal medication composed of bioactive herb extracts, active essential oils and combinations thereof.

It is another object of the invention to provide a medication for treatment of oral mucosal disorders in which the active agent is at least one bioactive safe herbal medicine adapted to be provided directly on the diseased site and to act as a physical barrier protection in addition to supplying suitable amounts of natural bioactive agent for an extended time period.

It is another object of the invention to provide a medication for treatment of oral mucosal disorders in which the active agent contain a homeopathic medication.

It is another object of the invention to provide a composition for treatment of oral mucosal disorders and aphthous stomatitis lesions which can stop progression of the lesion in any phase of its development.

It is another object of the invention to provide a composition and treatment for lesions induced by inflammation, various viruses and microbes and combination thereof.

It is another object of the invention to provide a composition and treatment for a wide variety of lesions caused by herpes viruses, allergic conjunctivitis and giant papillary conjunctivitis, stomatitis secondary to chemotherapy, second degree sunburn, third degree thermal burns, and aphthous stomatitis.

It is another object of the invention to provide a self bioadhesive solid confortable sticker that adheres to the oral mucose for a few hours, loaded with certain herbal compositions effective in treating oral lesions.

It is another object of the invention to provide a bioadhesive solid sticker loaded with a synergistic anti-aphthous combination of citrus oils containing at least 60% limonene and Carnallite salt.

It is another object of the invention to provide a bioadhesive solid sticker loaded with at least one bioactive monoterpene of three unsaturations including: limonene, myrcene, pinene, sabinene and the like.

It is another object of the invention to provide a bioadhesive sticker loaded with a mixture of a bioactive herbal medicine and a synthetic or natural bioactive anesthetic, analgesic, antiviral, antimicrobial, anti-inflammatory, anti-proliferative or antifungal agent or mixtures thereof including: local anesthetics of the caine family, nonsteroidal anti-inflammatory agents, antimicrobial quaternary amonium salts, chlorhexidine, amphotericine B, azole antifungals, and antibiotics.

It is another object of the invention to provide a bioadhesive solid disc comprising the bioadhesive composition, limonene as mucosal enhancer, a mixture of herbal extract and a synthetic or natural bioactive anesthetic, antiviral, antimicrobial, anti-inflammatory, anti-proliferative or antifungal agent.

It is another object of this invention to provide a solid medication for treating oral lesions that is prepared by compression molding of a powder using conventional tableting equipment.

Briefly described and in accordance with one embodiment thereof, the invention provides a composition and method of use for topical treatment of epithelial lesions for various herpes-caused lesions and various other lesions and inflammations such as aphthous stomatitis, stomatitis secondary to chemotherapy, photodermatitis, thermal burns, and decubitus ulcers in the oral cavity.

Thus, according to the present invention, there is now provided a solid, self-bioadhesive composition for topical application that adheres to the oral mucosal tissue comprising:

(a) a therapeutically effective amount of at least one herbal or homeopathic active agent; and (b) a pharmaceutically acceptable solid bioadhesive carrier in an amount from about 40 to 99 percent based on the weight of the whole composition.

In preferred embodiments of the present invention, the herbal active agent is selected from the group consisting of an either anti-inflammatory, analgesic, antiaching, anesthetic, antimicrobial, antifungal, antiseptic, antiviral, antibiotic, and an antiparasite agent and combinations thereof.

In especially preferred embodiments of the present invention, the herb essential oils active agents are selected from the group consisting of: citronella oil, lemon oil, citron oil, pomela peel oil, cedrwood oil, juniper berries oil, lemon basil oil, rosmarinus offencinalis oil, cinnamon oil, cajeput oil, eucalyptus oil, fennel oil, geranium oil, girofle oil, lavender oil, clove oil, spearmint oil, myrte oil, origano oil, pine oil, rosemary oil, sarriette oil, thyme oil, and tea-tree oil.

In a most preferred embodiment of the present invention, said essential oil comprises at least one monoterpene with three unsaturations.

In other preferred embodiments of the present invention, there is provided a solid, self-bioadhesive composition for topical application as hereinbefore defined and further comprising a non-herbal active agent selected from the group consisting of analgesics, steroidal and non-stroidal anti-inflammatory agents, antihistaminic or antiallergics, steroids, antimicrobial drugs, vitamins, enzymes, anti-allergic drugs, antipyretics, antimalarial, antiulcer drugs, peptides, DNA plasmid and antisense based therapeutic agents.

In another aspect of the present invention, there is provided a solid self-bioadhesive composition for a topical applicatin that adheres to the oral mucosal tissue comprising a combination of an anti-inflammatory agent and an anti-microbial agent; and a pharmaceutically acceptable solid bioadhesive carrier in an amount from about 40 to 99 percent based on the weight of the whole composition.

The invention also provides a method for the preparation of a solid, self-bioadhesive composition for topical application that adheres to the oral mucosal tissue comprising the following steps:
 i) forming a solid powder of a herbal active agent by drying the herbal liquid extract with an inert component;
 ii) mixing the herbal active powder with the adhesive inert powders and lubricants; and
 iii) compressing said mixture into tablets of the desired size and shape.

DETAILED DESCRIPTION OF PREFERRED EMBODIMENT OF THE INVENTION

Bioadhesive Compositions

Suitable adhesive carriers include any of the non-toxic polymers, particularly those of the type used to carry drugs including carboxylic acid coataining polymers such as copolymers of acrylic or methacrylic acid, copolymers of maleic acid, and polysacchrides such as, karaya gum, tragacanth gum, pectin, guar gum, alginates, hydrocolloid gels prepared from polysaccharides extracted from *Fronia elephantum, Sapindus trifoliatus*, Kunjac, and the cashew tree; cellulose, and cellulose derivatives such as methyl cellulose, propyl cellulose, cellulose acetate and the like, along with other substances known for use in transdermal preparations capable of forming a solid colloid that can adhere to tissue, used alone or in combination with other suitable carriers. A particularly preferred carrier is a bioadhesive for application to the mucosa composed of a mixtures of slightly crosslinked polyacrylic acid, i.e. Carbopol 940, 934, 974, and the like, carboxymethyl cellulose and hydroxypropylmethyl cellulose (HPMC).

The term "adhesive" as used herein means a substance, inorganic or organic, natural or synthetic, that is capable of surface attachment to the intended oral cavity application site.

The term "bioadhesive" as used herein means an adhesive which attaches and preferably strongly attaches to mucosal tissue upon hydration. Indeed, to qualify as a bioadhesive, a substance must be capable of maintaining adhesion in moist or wet in-vivo environments. The final composition of the present invention is "self-adhesive" in that it attaches to the site of interest without the need to reinforce its attachment by way of another adhesive which is applied to a backing.

The strength of adherence can be measured by standard tests for measuring the force, e.g. in dynes per square centimeter, as disclosed in U.S. Pat. No. 4,615,697. Suitable bioadhesives include those prepared from optionally partially esterified polyacrylic acid polymers, including but not limited to, polyacrylic acid polymers lightly crosslinked with a polyalkenyl polyether such as those commercially available from B.F. Goodrich, Cincinnati, Ohio, under the trademarks Carbopol 934, 934P, 974, 940 and 941.

Other suitable bioadhesives include natural or synthetic polysaccharides. Suitable polysaccharides include cellulose derivatives such as, cellulose acetate, carboxymethylcellulose, hydroxyethylcellulose and the like. Other suitable bioadhesives are pectin, a mixture of sulfated sucrose and aluminum hydroxide, hydrophilic polysaccharide gums such as natural plant exudates, including karaya gum, ghatti gum, tragacanth gum, xanthan gum, jaraya gum and the like, as well as seed gums such as guar gum, locust bean gum, psillium seed gum and the like. The term non-carrier refers to any liquid or semi liquid known for or suitable for use in pharmaceutical preparations as will be apparent to one skilled in the art.

In addition to the above ingredients, there may also be incorporated other additives selected from among the various pharmaceutically acceptable additives available to those skilled in the art. These additives include binders, stabilizers, preservatives, flavorings and pigments. In a preferred embodiment, the compositions of the present invention also contain a binder such as lecithin which "binds" the other ingredients, thereby enhancing the uniform consistency of the final composition.

The composition of this invention is administered in appropriate sizes, typically having a surface area of from about 0.4 to about 3 cm.sup.2 or conveniently 0.5 to 1.2 cm.sup.2. The active agent is loaded into the composition in as high a concentration as necessary to effect therapy, e.g., in a range from about 0.1 mg/cm.sup.2 to about 50 or more mg/cm.sup.2.

In general, the composition can have the following types and amounts of ingredients:

| Ingredient | Typical Range (% by weight) | Preferred Range (% by weight) | Optimum Range (% by weight) |
| --- | --- | --- | --- |
| Adhesives | 15 to 99 | 50 to 95 | 70 to 95 |
| Additives | 0.1 to 10 | 0.1 to 5 | 0.1 to 5 |
| Actives | 0.1 to 50 | 1 to 30 | 1 to 20 |

In one embodiment, the flexible, bioadhesive composition for topical application comprises a therapeutically effective amount of at least one herb extract for treating an oral disorder; and a bioadhesive carrier composition in a defined predetermined size that sticks to the buccal surface and stays in the site for at least 30 min. The carrier composition may contain an acceptable plasticizer for the bioadhesive, and a cohesive agent.

Preparation of a Herbal Agent for Use in the Sticker Formulation

Because of the limited size of the device to be applied and the loading, the active agent should be concentrated to include as much active agent as possible. In addition, because the device is prepared by molding of a powder mixture in a tableting machine, it is essential that the composition will be in a free flowing powder form suitable in use with commercial tableting devices. Thus the active herbal agents should be condensed into a concentrated powder. Usually, hydroalcoholic herb extracts when dried from the solvents, form a sticky mass that can not be incorporated homogeneously as flowing powder with the inert ingredients. Also, if essential oils are used as active agents they should be converted into powder. To overcome this limitation, we have developed a method in which the active agents are absorbed into an inert free flowing powder at a high concentration which is then mixed with the bioadhesive ingredients to form a free flowing powder prior to press molding.

Typically, a water soluble pharmaceutically acceptable component such as a sugar is added to the herb extract solution, which after freeze-drying forms a powder. The amount of loading is given in terms of the amount equivalent to the dry weight in grams of the extracted plant per gram of inert absorbent material (sugar). For example, 2 g mannitol is dissolved into a given tincture of 100 ml prepared from the extraction of 10 g of plant and lyophilized to dryness to form a powder which weigh 2.5 grams. Each gram of this powder is equivalent to 4 gtrams of plant extract.

When essential oil to be incorporated in the sticker, the oil is absorbed in a suitable powdery absorbent. Typical absorbents include for example, kaoline, Kapectin, alumina, silica, polystyrene beads, polyacrylate beads, clay, microcrystalline cellulose, and other orally acceptable powders with oil absorption capacity. The use of a crude herbal material that is part of the bioactive agents in a powder form is used for oil absorption.

The typical process of preparing of Crude Herbal Material for Extraction is as follows:

1. Crude dry herbal materials are milled into fine powders using a proper milling device. Any grinding operation that achieves the respective particle size for extraction is acceptable. Technical reason for milling step is to have a consistently-sized crude herb powder. Crude herb extractibility is a critical function of exposed surface area of crude herb powder to hydroalcoho mass ratio. To eliminate crude herb particle size as a process variable and since the various herbs have different water-holding capability (porosity/absorptivity), a singular particle size is preferred for process control. Depending on the specific type of crude herbs, milling produces a mix of coarse and fine dust particulates.

2. All milled crude herb powders are mixed in a blender to provide uniform particle size of crude herbs prior to extraction. Particle size of milled crude herbal powder is consistent following this step.

3. Crude Herbal Material Extractions in hydroalcoholic solution (Either option is suitable)

a.) Soxhlet option: About 1-60 parts of milled crude herbal powder are added to 100-5000 parts (process and/or deionized or equivalent grade) water:alcohol in a Soxhlet Extractor and then decanted. A Soxhlet extractor is one or more station continuous reflux extractor with internal condenser slowly feeding 4.degree.-100.degree. C. solution across the herb for up to 48 hours.

b.) Ultrasonics option: Suitable alternate extraction process for developing this water soluble extract include use of ultrasonic water extraction systems which can provide equivalent quality, depending on the herb, with up to 94% faster process cycles, hydrolysis extracting reactors, fixed bed extracting reactors, desorption extraction columns, and countercurrent extractors. Due to most commercial extraction process limitations, it is normal to have a small amount of particulates in this extract.

4. Water-extracted herbal liquid is filtered (e.g., 5-100.mu.filter cartridge, fine screen or cheesecloth) or centrifuged to remove coarse and/or insoluble particulates.

5. Filtered water-extracted herbal liquid is concentrated, depending on herbal ingredient, up to a 50% soluble solids level. In addition to concentration by evaporation, alternate suitable process to achieve higher concentrations prior to final drying include freeze concentration, partial freeze drying, membrane separation, vacuum distillation and vacuum drying.

6. Concentrated herbal extract liquids are dried via commercial drying processes. Suitable dryers that are used include fluidized bed, vacuum plate, spray, drum-type and flash dryers. Drying efficiency is controlled for water content (<10%) and free water considerations (.Itoreq.0.80) to achieve shelf-stability. Yield of soluble powder from the drying process is used as key to optimize herb: water mass formula for extraction.

7. Dried pure solid herbal extract powders are sized and packaged for shipment. A dessicating-materials such as a silica gel or other suitable FDA-approved, drying agent can be used to control relative humidity and to improve shelf-life.

8. Dried pure solid herbal extract powder is now ready for reconstitution into oral care products.

The Active Agents on this Invention:

The present invention relates to compositions and methods of treating or preventing diseases of the oral cavity in humans- or animals, by applying to the oral cavity, a safe and effective amount of a herbal medication composed of herbal extracts that have anesthetic, antiviral, antiinflammatory, intiproliferative, antibacterial or antifungal activity. Of particular interest are active essential oils and plant extracts including: citronella oil, lemon oil, citron oil, cedrwood oil, juniper berries oil, lemon basil oil, rosmarinus offencinalis oil, cinnamon oil, cajeput oil, eucalyptus oil, fennel oil, geranium oil, girofle oil, lavender oil, clove oil, spearmint oil, myrte oil, origano oil, pine oil, rosemary oil, sarriette oil, thyme oil, and tea-tree oil. Most preferably, the essential oil is selected from the group consisting of cinnamon oil, tea-tree oil and citronella oil. Preferably, the essential oil is present at a concentration of from about 0.02 to about 90 percent weight per weight of the active agent composition, and most preferably from about 5 percent to about 50 percent weight per weight.

According to further preferred features of the present invention, the tincture includes a material selected from the group consisting of Plantago, Hypericum, Echinacea, Baptisia, Calendula, Myrrah, Phytolaca, *Salvia*, Catechu black, Coneflower, *Krameria*, Tsuga, grape fruit seed extract, Rosmarinus, Styrax, Crataegus, Glycerrhiza, Angelica, *Krameria*, Matricaria, Mallow, Propolis and Sage. Barberine from hydrastis canadensis L. and other berberidaccae plant family, gentian from the gentianaceae family of plants for the treatment of fungal infections, monoterpenes of three unsaturations, *Taraxacum* extract, *Lonicera* flower extract, *Scutellaria* root extract, *Gardenia* fruit extract, *Pulsatilla* root extract, *Pueraria* root extract, *Radix gentianae* Longdancao antifungal agent to treat cutaneous and mucosal syndromes caused by candida infection or plant extract selected from the combination of two or more of those and other herbal bioactive agents.

The prior art also discloses dentifrices containing herb medicine extracts known to be suppressive of the formation of plaque, as disclosed in Korean Pat. Appln. No. 93-9048 to the present applicant, Korean Pat. Publication No. 91-1919, Korean Pat. Publication Laid-Open No. 91-18007, Japanese Pat. Publication Laid-Open Nos. Sho 56-83415, Sho 57-58610, Sho 57-58611, Sho 57-58612, Sho 57-58513, Sho 57-56415, Sho 59-152313 and Hei 1-151512, and Japanese Pat. Publication Nos. Hei 3-66283 and Hei 3-32524. Most of the herb medicine extracts described in the above-cited patents contain considerable amounts of coloring materials in addition to pigments. When these herb medicine extracts are used for striped toothpastes, the bleeding of the coloring materials or pigments readily occurs in the existing toothpaste formulations.

In particular, Korean Pat. Appln. No. 93-9048 discloses an invention that relates to products for oral cavities, such as plaque formation inhibiting toothpaste, mouthwash, chewing gum, and gingival massage cream. More specifically, selected plaque formation inhibiting ingredients includes *Taraxacum* extract or, other than *Taraxacum* extract, *Lonicera* flower extract, *Scutellaria* root extract, *Gardenia* fruit extract, *Pulsatilla* root extract, *Pueraria* root extract or plant extract selected from the combination of two or more of those. Korean Pat. Appln. No. 93-9048 thus discloses a composition for oral cavity that includes *Taraxacum* extract as plaque formation inhibiting ingredient. Furthermore, the reference discloses a composition for oral cavity that includes, other than *Taraxacum* extract, *Lonicera* flower extract, *Scutellaria* root extract, *Gardenia* fruit extract, *Pulsatilla* root extract, *Pueraria* root extract or plant extract selected from the combination of two or more of those.

Plant extracts are also disclosed that are obtained from the following plants: *Taraxacum* used is the whole plant body of *Taraxacum platycarpum* H, *Dahlstedt* or Carduaceae, and has antibiotic and anti-Eumycetes effect, therefore, it is used in eastern medicine for many kinds of inflammation; *Lonicera* flower used is the flower of *Lonicera japonica* Thunberg, and has antibiotic, antivirus, anti-Eumycetes and astringent effect, therefore, it is used in eastern medicine for inflammation in mouth, bleeding caused by inflammation, and swelling and used as general inflammation medicine when combined with *Taraxacum; Scutellarai* root is peeled root of *Scutellaria baicalensis* Georgi and has antibiotic, antivirus, anti-Eumycetes and sedative effect, therefore, it is used in eastern medicine for inflammation, tooth ache, oral cavity ache, tooth decay, and periodontitis by combining with *Gardenia* and etc.; *Gardenia* fruit used is a fruit of *Gardenia jasminoides* Ellis tree or Rubia Akane and has stopping of bleeding, antibiotic and sedative effect, therefore it is used in eastern medicine for many kinds of inflammation including inflammation inside a mouth and bleeding caused by inflammation; *Pulsatilla* root used is a root of *Pulsatilla koreana* Nakai or Carduaceae and has antibiotic, anti-Eumycetes and astringent effect, therefore, it is used in eastern medicine for tooth ache and many kinds of inflammation; and *Pueraria* root is a peeled root of *Pueraria thunbergiana* Bentham and has pain-alleviating and anti-inflammation effect, therefore, it is used in eastern medicine for tooth ache and inflammation inside of mouth by combining with *Scutellaria* root and etc.

Extracts from medicinal herbs which are known to be suppressive of the formation of plaque may be contained in adhesive sticker, that is, the striped dentifrice component of the composition according to the present invention, the concrete examples of which are described in Korean Pat. Appln. No. 93-9048, Korean Pat. Publication No. 91-1919, Korean Pat. Publication Laid-Open No. 91-18007, Japanese Pat. Publication Laid-Open Nos. Sho 56-83416, Sho 57-58610, Sho 57-58611, Sho 57-58612, Sho 57-58513, Sho 57-56415, Sho 59-152313 and Hei 1-151512, and Japanese Pat. Publication Nos. Hei 3-66283 and Hei 3-32524. Of them, preferred are the materials extracted from *taraxacum, gardenia, lonicera, scutellaria, pulsatilla* and/or *pueraria*.

By the term "monoterpenes of three unsaturations" as used herein, is meant a composition containing at least one monoterpene of three unsaturations of the molecular formula $C_{10}H_{16}$, wherein unsaturation in chemistry is a double bond or a cyclization. Examples are limonene containing two double bonds and one cyclic group, myrcene contains three double bonds, sabinene, a-pinene and b-pinene.

Compositions containing limonene, monoterpenes of three unsaturations, among a list of components have been mentioned in the prior art. For example, U.S. Pat. No. 5,453,276 lists limonene among anacerdic acid, farnesol, citronellol, pine resin, hinokitiol, longifolene and caryophyllene that together showed antimicrobial activity. U.S. Pat. Nos. 5,279,813, 5,273,741, 5,234,688, 5,167,951, describes antiplaque compositions containing triclosan as antibacterial agent and polyphosphate for anti-tartar actions. In these compositions, limonene was used as stabilizer. U.S. Pat. No. 5,925,335 describes toothpaste formulations containing Vitamin C and ubiquinone as active agents with a small amount of limonene as flavoring agent. U.S. Pat. No. 5,939,050 mentions lemon oil among other oils that in combination with other oils may posses and antimicrobial activity. U.S. Pat. No. 5,910,455 mentions limonene as an abrasive hand cleansing material in a cleanser compostion. Limonene is also mentioned in U.S. Pat. No. 5,079,063 as antiflea agent for making flea-free carpets. Limonene is also described in U.S. Pat. No. 5,164,416 as skin penetrating enhancer in transdermal formulations. All of the above references are incorporated herein by reference in their entirety.

The above prior art references have not recognized that the topical delivery of monoterpenes with three unsaturations to the oral cavity will provide efficacy in various oral care conditions. Therefore, prior art compositions, mentioned above, have not been entirely satisfactory for the treatment and/or prevention of oral mucosal lesions. Therefore, additional efficacious compositions and methods of treatment for these purposes are desirable.

In accordance with the present invention, new formulations and treatments have been discovered which, when applied topically to the viral diseases herpes labialis (cold sores or fever blisters), herpes genitalis, herpes zoster (shingles), varicella zoster (chickenpox); inflammatory diseases and or diseases demonstrating compromise or reaction of the immune system including aphthous stomatitis (canker sores), oral mucositis (stomatitis) secondary to chemotherapy, allergic conjunctivitis, giant papillary conjunctivitis; and lesions of injury to the skin including photodermatitis (sunburn, specifically second degree sunburn), thermal burns and pressure sores (decubitus ulcers), have been found to be very effective in either preventing lesions from occurring, minimizing the severity of lesions that are formed, or mitigating the duration and pain from such lesions already developed. Clinical studies indicates that if the medication of the present invention is applied initially when symptoms of a lesion or inflammatory reaction are first developing (when numbness, prickling sensation, itching, etc. are experienced), subsequent phases of the lesion or inflammatory reaction do not develop or develop to a lesser degree than would otherwise be seen.

Another optional component of the topical, oral sticker of the compositions of the subject invention is a humectant which acts as a plasticizer to provide a flexible and comfortable sticker, generally comprises from about 1% to about 20%, preferably from about 1% to about 5%, by weight of the compositions herein. Suitable humectants for use in compositions of the subject invention include edible polyhydric alcohols such as glycerin, sorbitol, xylitol, butylene glycol, polyethylene glycol, and propylene glycol, especially sorbitol and glycerin.

Flavoring agents can also be added to the compositions. Suitable flavoring agents include oil of wintergreen, oil of peppermint, oil of spearmint, clove bud oil, menthol, anethole, methyl salicylate, eucalyptol, cassia, 1-menthyl acetate, sage, eugenol, parsley oil, oxanone, alpha-irisone, marjoram, lemon, orange, propenyl guaethol, cinnamon, vanillin, thymol, linalool, cinnamaldehyde glycerol acetal known as CGA, and mixtures thereof. Flavoring agents are generally used in the compositions at levels of from about 0.001% to about 1%, by weight of the composition.

Sweetening agents which can be used include sucrose, glucose, saccharin, dextrose, levulose, lactose, mannitol, sorbitol, fructose, maltose, xylitol, saccharin salts, thaumatin, aspartame, D-tryptophan, dihydrochalcones, acesulfame and cyclamate salts, especially sodium cyclamate and sodium saccharin, and mixtures thereof. A composition preferably contains from about 0.1% to about 2% of these agents, preferably from about 0.1% to about 1%, by weight of the composition.

In addition to flavoring and sweetening agents, coolants, salivating agents, warming agents, and numbing agents can be used as optional ingredients in compositions of the present invention. These agents are present in the compositions at a level of from about 0.001% to about 10%, preferably from about 0.1% to about 1%, by weight of the composition. The coolant can be any of a wide variety of materials. Included among such materials are carboxamides, menthol, ketals, diols, and mixtures thereof.

Preferred salivating agents of the present invention include Jambus® manufactured by Takasago. Preferred warming agents include capsicum and nicotinate esters, such as benzyl nicotinate. Preferred numbing agents include benzocaine, lidocaine, clove bud oil, and ethanol.

For the method of treating diseases or conditions of the oral cavity of the present invention, a safe and effective amount of herbal composition is preferably applied to the gingival/mucosal tissue in a form on a bioadhesive sticker preferably for at least 30 min., preferably from about 1 hour to about 24 hours, more preferably from about 3 to about 10 hours. The method often involves expectoration of most of the composition following such contact. The frequency of such contact is preferably from about four times per day or once per day, more preferably from about once per day to about twice per day. The period of such treatment typically ranges from about one day to a 7 days. For particular oral care diseases or conditions the duration of treatment depends on the severity of the oral disease or condition being treated, the particular delivery form utilized and the patient's response to treatment.

While the invention will now be described in connection with certain preferred embodiments in the following examples so that aspects thereof may be more fully understood and appreciated, it is not intended to limit the invention to these particular embodiments. On the contrary, it is intended to cover all alternatives, modifications and equivalents as may be included within the scope of the invention as defined by the appended claims. Thus, the following examples which include preferred embodiments will serve to illustrate the practice of this invention, it being understood that the particulars shown are by way of example and for purposes of illustrative discussion of preferred embodiments of the present invention only and are presented in the cause of providing what is believed to be the most useful and readily understood description of formulation procedures as well as of the principles and conceptual aspects of the invention.

Example 1

Preparation of Herb Extract Powder

The herb medicine extracts were obtained by adding 30 g of each of sliced and dried a herb group comprising *Taraxacum platycarpum* H. Dahlstedt, *Gardenia jasminoides* Ellis, *Lonicera japonica* Thunberg, *Scutellaria baicalensis* Georgi, *Pulsatilla koreana* Nakai and *Pueraria thumbergiana* Bentham, in a solvent mixture comprising 300 ml of each of water and ethanol, shaking or refluxing for 3 hrs. to extract medicinally useful substances, passing the solution through a filtering paper, centrifuging the filtered solution, and decanting the solution. Sugar powder (mannitol or dextrose) is added (1 gram of sugar per 10 gram equivalent of dry plant), and freeze dry the solution to obtain a fine flowing powder. The amounts of the obtained herb medicine extracts in ethanol on the basis of dry solid substance is: 6.2, 9.4, 7.7, 7.7, 9.2 and 9.5 gram, respectively. Other plant extract powders were prepared similarly by adding to the extract solution an inert component such as sugars, microcrystalline cellulose, titanium dioxide, silicone dioxide, talk, and other inert powders. All calculations for the active agent were based on the dry plant.

Preparation of Oil Powder

Essential oil, limonene, and other oils to be incorporated in the sticker were absorbed into absorbing powders including talk, microcrystalline cellulose, titanium dioxide, silicone dioxide, polystyrene beads, methacrylates and other pharmaceutically acceptable solid powders with absorption capacity. In a typical experiment, 1 g or the following oils: limonene, pinenes, myrcene, terpinene, citron oil, orange oil, mint oil, clove oil, lemone oil, and pumela oil, were mixed with 2 grams of talk, hydroxypropyl methyl cellulose (HPMC), or silicone dioxide. After about one hour a free flowing powder was obtained.

Example 2

Preparation of Tablets

Tablets were prepared as described in the following table. Usually, by directly compressing of polymer mixture and magnesium stearate as the first layer (10 mg), and the active ingredient (freeze-dried) and polymer mixture (50 mg) as second layer. The tablets were prepared with tabulating press pressures dye (3, 7 or 10 ton) for 30 second using a die 10 or 5 mm in diameter.

TABLE 1

| Tablets index | Polymers mixture | Active ingredients (freeze dried) | Tablet ingredients | Number Diameter pressure |
|---|---|---|---|---|
| AD-2-B | 2 g of Carbopol 934 + 1 g of HPC (AD-2-C) | Echinacea, 1:1, 70% (1.5 ml) Elder, 1:5, 70% (35 ml) Gotu-kola, 1:4 15% (6 ml) Sugar, 2 g (AD-2-A) | A mixture of 2 g AD-2-C and 0.2 g AD-2-A. Tablet weight = 50 mg | 25 tablets 10 mm 10 ton |

TABLE 1-continued

| Tablets index | Polymers mixture | Active ingredients (freeze dried) | Tablet ingredients | Number Diameter pressure |
|---|---|---|---|---|
| AD-1-C Control | 2 g of Carbopol 934 + 1 g of HPC (AD-2-C) | — | AD-2-c<br>Tablet weight = 50 mg | 10 tablets<br>10 mm<br>10 ton |
| AD-3-A | 2 g of Carbopol 934 + 1 g of HPC (AD-2-C) | Bendocaine, 10% (0.2 g)<br>Camalit 10%, (0.2 g) | Bendocaine, 10% (0.2 g)<br>Oil, 2% (0.04 g)<br>Camalit 10%, (0.2 g)<br>Polymers mixture, (AD-2-C) 78% (1.56 g)<br>Tablet weight = 50 mg | 32 tablets<br>10 mm<br>10 ton |
| AD-4-A Control | 2 g of Carbopol 934 + 1 g of HPC (AD-2-C) | — | AD-2-C<br>Tablet weight = 50 mg | 40 tablets<br>10 mm<br>10 ton |
| AD-4-B Control | 2 g of Carbopol 934 + 1 g of HPC (AD-2-C) | — | A mixture of 1 g AD-2-C and 1 g magnesium stearate (10 mg, layer I) + 50 mg of AD-2-C (layer II).<br>Tablet weight = 60 mg | 30 tablets<br>10 mm<br>10 ton |
| AD-6-B | 2 g of Carbopol 934 + 1 g of HPC (AD-2-C) | Echinacea, 1:1, 70% (1.5 ml)<br>Elder, 1:5, 70% (35 ml)<br>Gotu-kola, 1:4 15% (6 ml)<br>Sugar, 2 g (AD-2-A) | A mixture of 1 g AD-2-C and 1 g magnesium stearate (10 mg layer I) +<br>A mixture of 1 g AD-2-A and 0.1 g AD-2-C (50 mg layer II).<br>Tablet weight = 60 mg | 25 tablets<br>10 mm<br>10 ton |
| AD-8-A Control | 2 g of Carbopol 934 + 1 g of HPC (AD-2-C) | | A mixture of 1 g AD-2-C and 1 g magnesium stearate (10 mg, layer I) + 50 mg of AD-2-C (layer II).<br>Tablet weight = 60 mg | 35 tablets<br>10 mm<br>10 ton |
| AD-9-C | 2 g of Carbopol 934 + 1 g of HPC (AD-2-C) | Echinacea, 1:1, 15% (1.5 ml)<br>Gotu-kola, 1:4 15% (6 ml)<br>Sugar, 2 g<br>After freeze drying 7 gr of Grape extract was added. (AD-9-B) | A mixture of 1 g AD-2-C and 1 g magnesium stearate (10 mg, layer I) +<br>A mixture of 1 g AD-2-C and 0.1 g AD-9-B (50 mg, layer II).<br>Tablet weight = 60 mg | 21 tablets<br>10 mm<br>10 ton |
| AD-13-B | 2 g of Carbopol 934 + 1 g of HPC (AD-2-C) | Bendocaine, 10% (0.4 g)<br>Oil, 2% (0.08 g)<br>Camalit 10%, (0.4 g) (AD-13-A) | A mixture of 1 g AD-2-C and 1 g magnesium stearate (10 mg, layer I) + 70 mg AD-13-A<br>Tablet weight = 80 mg | 30 tablets<br>10 mm<br>10 ton |
| AD-13-C | 2 g of Carbopol 934 + 1 g of HPC (AD-2-C) | Bendocaine, 10% (0.4 g)<br>Oil, 2% (0.08 g)<br>Camalit 10%, (0.4 g) (AD-13-A) | A mixture of 1 g AD-2-C and 1 g magnesium stearate (5 mg, layer I) + 50 mg AD-13-A<br>Tablet weight = 55 mg | 30 tablets<br>5 mm<br>3 ton |
| AD-18-a | 2 g of Carbopol 934 + 1 g of HPC (AD-17-a) | Bendocaine | A mixture of 100 mg AD-17-a and 10 mg bendocaine (layer I) + a mixture of 1 g AD-17-a and 1 g magnesium stearate (20 mg, layer II)<br>Tablet weight = 130 mg | 5 tablets<br>10 mm<br>10 ton |
| AD-18-B | 2 g of Carbopol 934 + 1 g of HPC (AD-17-a) | Plants extract? | Mixture of 100 mg AD-17-a and 10 mg Plants extract? (layer I) + a mixture of 1 g AD-17-a and 1 g magnesium stearate (20 mg, layer II) | 5 tablets<br>10 mm<br>10 ton |
| AV-19-g | 2 g of Carbopol 934 + 1 g of HPC (AV-19-c) | Echinacea 1:1, 20% (2 ml)<br>Elder, 1:5, 15% (7.5 ml)<br>Myrrh, 1:4, 20% (8 ml)<br>Hypericum 1:10, 20% (20 ml)<br>Uncaria, 1:4, 25% (10 ml)<br>Sugar, 2 g (AV-19-b) | A mixture of 1 g AV-19-c and 1 g magnesium stearate (10 mg, layer I) + a mixture of 1 g AV-19-c and 0.1 g AV-19-b (50 mg, layer II). | 20 tablets<br>10 mm<br>7.5 ton |
| AV-19-f Control | 2 g of Carbopol 934 + 1 g of HPC Av-19-c) | — | | 10 tablets<br>10 mm<br>7.5 ton |
| AV-20-g | 2 g of Carbopol 934 + 1 g of HPC | Echinacea 1:1, 70% (1.5 ml)<br>Elder, 1:5, 70% (35 ml)<br>Gotu-kola, 1:4 15% (6 ml) | A mixture of 1 g AV-19-c and 1 g magnesium stearate (10 mg, layer I) + | 40 tablets<br>10 mm<br>7.5 ton |

TABLE 1-continued

| Tablets index | Polymers mixture | Active ingredients (freeze dried) | Tablet ingredients | Number Diameter pressure |
|---|---|---|---|---|
| | (AV-19-c) | Sugar, 2 g (AV-20-a) | a mixture of 2 g AV-19-c and 0.2 g AV-20-a (50 mg, layer II). Tablet weight = 60 mg | |
| AV-20-e | 2 g of Carbopol 934 + 1 g of HPC (AV-19-c) | Echinacea, 1:1, 1.5 cc Gotu-kola, 1:4, 6 ml Sugar, 2 g (AV-20-b) | A mixture of 1 g AV-19-c and 1 g magnesium stearate (10 mg, layer I) + a mixture of 1 g AV-19-c and 0.1 g AV-20-b (50 mg, layer II). Tablet weight = 60 mg | 20 tablets 10 mm 7.5 ton |

This composition then was applied topically to various types of lesions, as subsequently described. In some formulation propylparaben or methylparaben at about 0.1% were used as a preservative. In other tablets, a plasticizer, polyethylene glycol, Mw=400, 1,000 and 5,000, tributyl citrate, dibutyl phthalates, or an unsaturated fatty acid or alcohol or fatty acid ester were added to produce a more pliable tablet.

Example 3

Preparation of Tablets by Various Methods

The simplest method for preparing the tablets is by compression tablets using a press machine, single or multi punch. The powder of the final formulation is loaded in the punch of different diameters ranging from 4 to 15 mm and thickness of about 0.5 mm to 2.5 mm. The thickness is defined by the amount of powder added, usually 50 mg to about 250 mg. Another way of preparing thin stickers is by casting a concentrated suspension in ethanol of all tablet ingredients onto a flat surface which after solvent evaporation, a thin sheet is obtained. The sheet is then cut into the desired size and shape using a cutting mold. The concentrated suspension can be molded into a mold of the desired shape that after solvent evaporation the device is obtained. These methods were used in this study, however, the easiest and cost effective method is compression molding of powder. To block one side of the tablet for the purpose of obtaining one side adhesion and release, an inert hydrophobic non-adhesive coating was applied. For compression tablets, a double compression was used where the inert powder was first added to the punch to cover the surface. The formulation powder is added on top and compression is applied to produce a tablet with one side less water permeable and non-sticking. Typical hydrophobic powders suitable for this coating include: fatty acids and salts such as Mg- or Ca-stearate, triglycerides and fatty acid esters, ethyl cellulose, methyl methacrylate-methacrylic acid copolymers (Eudragit), and other pharmaceutically acceptable hydrophobic components. To improve the adherence between the coating and the tablet, the hydrophobic components are mixed with the carrier components, i.e. HPMC and Carbopol at a ratio of 30 to 70% by weight. Alternatively, single layer tablets were prepared and the coating on one side was applied by spray coating of the tablet on one side with an alcoholic solution or fine dispersion of the hydrophobic coating. The spray coating of one side can be applied on the automated machine where the tablets are placed onto a running sheet which is exposed to spray nozels to spray coat the tablets. If solvent cast method of preparation is used, the coating can be applied as a spray on top of the sheet loaded with the active agents. Other industrial methods can be applied including forming the sheet on an edible hydrophobic sheet such as rise paper and cut to devices.

In a typical experiment, 15 mg of white powder composed on 50% Mg-stearate, 33% Carbopol 934, and 17% HPMC, is added to laboratory punch and slightly rotated to obtain a uniform surface, on top of this, 70 mg of a mixture composed of 7 mg of plant extract and 63 mg of a powder mixture of Carbopol 934, HPMC (2:1 weight ratio). The powder was compressed into a tablet at a pressure of 7 tons per sq. cm for 30 seconds. Uniform strong dark tablet with a white coating on one side were obtained.

A multi layer sticker was prepared by compression of three different powders, the first layer is a thin layer of self adhesive powder, Carbopol 934: HPMC 2:1 w/w ratio loade with benzocaine local anesthetic for initial pain relief, the second layer is loaded with the herbal active agents and the third layer is a capping layer of a hydrophobic less water soluble layer. The main advantage of using a multilayer tablet is that each layer may contain different active agents that are exposed at a different time and rate to the mucosal surface for better treatment.

Components that have been tested for inert self-bioadhesive polymer include: mixture of carboxymethyl cellulose, polyacrylic acid, and crosslinked arabinogalactan and dextran and polyethylene glycol that form a complex with the carboxylic acid residues of acrylates.

Example 4

Preparation of Herbal Sticker with Antimicrobial and Anti-inflammatory Activity

Tablets were prepared by compression molding of herbal active composition in powder form and mixtures of Carbopol 940 and HPMC and other inert ingredients:
Herbal Ingredients:

| Ingredient | activity |
|---|---|
| Echinacea | analgesic, anti-inflammatory, antimicrobial |
| Calendula | anti-inflammatory |
| Grapefruit seed extract | anti-fungal, antibiotic |
| Blood root | antibiotic, anti-inflammatory |
| Goldenseal | antiseptic, antibiotic |
| Aloe vera | analgesic, anti-inflammatory |
| Bee propolis | anti-inflammatory, antibacterial |

These herbal extracts with a concentration of 1 ml equivalent to 1 gram of dry plant were mixed together at equal volumes, mannitol was added at a 1 g per 10 g of dry plant equivalent to provide a powdery material and lyophilized to dryness. A dark dry powder was obtained which was used for tableting. The following compositions were prepared:
1. all ingredients at equal ratio equivalent to dry plant
2. Echinacea, Calendula and Grapefruit at equal ratio
3. Echinacea, Calendula and oldenseal at equal ratio These powders were mixed with inert powder with or without other bioactive agents and formed tablets. The following compositions were compressed into 80 mg tablets:

| a. | Herbal powder 1 | 10 mg |
|---|---|---|
| | Carbopol 934 | 50 mg |
| | HPMC | 25 mg |
| | Mint extract | 5 mg |

The cap coating composed of a mixture of 5 mg of Mg-stearate and 5 mg Carbopol:HPMC 2:1 w/w.

| b. | Herbal powder 2 | 10 mg |
|---|---|---|
| | Carbopol 934 | 50 mg |
| | HPMC | 25 mg |
| | Mint extract | 5 mg |

The cap coating composed of a mixture of 5 mg of Mg-stearate and 5 mg Carbopol:HPMC 2:1 w/w.

| c. | Herbal powder 3 | 30 mg |
|---|---|---|
| | Carbopol 934 | 40 mg |
| | HPMC | 20 mg |
| | Mint extract | 5 mg |

The cap coating composed of a mixture of 5 mg of Mg-stearate and 5 mg Carbopol:HPMC 2:1 w/w.

| d. | Herbal powder 1 | 10 mg |
|---|---|---|
| | Benzocaine | 10 mg |
| | Carbopol 934 | 50 mg |
| | HPMC | 25 mg |
| | Mint extract | 5 mg |

The cap coating composed of a mixture of 5 mg of Mg-stearate and 5 mg Carbopol:HPMC 2:1 w/w.

| e. | Herbal powder 1 | 10 mg |
|---|---|---|
| | Lidocaine | 5 mg |
| | Carbopol 934 | 50 mg |
| | HPMC | 25 mg |
| | Mint extract | 5 mg |

The cap coating composed of a mixture of 5 mg of Mg-stearate and 5 mg Carbopol:HPMC 2:1 w/w.

| f. | Herbal powder 1 | 10 mg |
|---|---|---|
| | Amphotericine B | 3 mg |
| | Carbopol 934 | 50 mg |
| | HPMC | 25 mg |
| | Nana flavor | 5 mg |

The cap coating composed of a mixture of 5 mg of Mg-stearate and 5 mg Carbopol:HPMC 2:1 w/w.

| g. | Herbal powder 1 | 10 mg |
|---|---|---|
| | dextranase enzyme | 320,000 units |
| | Carbopol 934 | 50 mg |
| | HPMC | 25 mg |
| | Mint extract | 5 mg |

The cap coating composed of a mixture of 5 mg of Mg-stearate and 5 mg Carbopol:HPMC 2:1 w/w.

| h. | Herbal powder 3 | 10 mg |
|---|---|---|
| | vancomicin | 1 mg |
| | Carbopol 934 | 50 mg |
| | HPMC | 25 mg |
| | Mint extract | 5 mg |

The cap coating composed of a mixture of 5 mg of Mg-stearate and 5 mg Carbopol:HPMC 2:1 w/w.

The above preparations were used by patients exhibiting herpetic stomatitis lesions (fever blisters or cold sores) and three patients with aphthous ulcers (canker sores), mucosal inflammation, toothache, RAS, and lesions on the lips, tang, and gingiva. Treatment consisting of topical application of the medication once a day at the lesion site resulted in a significant improvement within 2-3 days of placing the stickers. In all cases the sticker remains on the site for at least 6 hours with slowly dissolution of the device.

Example 5

Sticker Composition and Testing

Tablets were prepared by directly compressing of polymer mixture (Carbopol 934+HPC, 1:2) and magnesium stearate (1:1) as the first layer (15 mg), and the active ingredient (freeze-dried) and polymer mixture (70 mg) as second layer. The tablets were prepared with tabulating press pressures (7 ton) for 30 second using a die 10 mm in diameter.

Active ingredient (equivalent to dry plant): Poder of the active ingredients was prepared by freeze dry a mixture of paint extrant at the amount equivalent to the dry plant: Chamomil 2 g, *Salvia* 2 g, Myrrh 1 g, Hypericum 1 g, and Mentha 0.4 g. To the mixture, Commiphoria powder 10%, 20 mg, and Mannitol 1 g were added and the the mixture was freeze dried to form 3.254 g of dark powder. For the preparation of each tablet, 15 mg of the mixture was taken.

The tablets were given to 10 patients suffering from significant recurrent aphthous lesions, 15 tablets each per treatment with instructions to place a sticker twice a day, morning and evening onto the lesion. After one day, the patients were highly satisfactory and reported an improvement with the lesions disappear in three days.

Example 6

Clinical Study on Essential Oil Loaded Stickers

Stickers loaded with Carnallite and citron oil and benzocaine as active agent, tablets AD-3-A in table of Example 1) were used for treating 17 patients with recurrent aphthous stomatitis (RAS) by applying a sticker twice a day onto the lesion. These patienats suffer from aphtous ulcers a few times during a month with one to three lesions each time.

The results were outstanding, for all patients, the sore and pain was eliminated within three houtrs and the elimination of the lesion within 24 hours. When the patients used the stickers for several weeks, in eleven patients the lesions did not resume for at least two month. The other six patients benefited from the device that the time period between lesion formation was increased to 6 weeks with a much milder episodes. It should be noted that all patients responded extremely well to the device with high compliance.

Similar tablets loaded with amphotericine B as antifungal agent was prepared in a similar way and applied on patients suffering from oral fungal infection with large lesions. In all cases an improvement was recognized two days after twice a day applications. Other natural and synthetic antifungal agents are used instead of amphotericine B such as Clotremazole, and Intraconazole.

In an another study, a 6-month trial was carried out, utilizing stickers loaded with the following composition: the three following components and combinations thereof:

Limonene, 92% of a citron peel essential oil, Carnallite salt, and Plant extracts of *Salvia (fruticosa)* and Junjerus. Limonene was prepared from citron leaves and the citron outer peel boiled in water (100° C.) for up to one minute, crushed in blender and filtered. The essential oil was separated and analyzed by Gas chromatograpy to determine its composition: The following components were found, limonene—92%, myrcene—2.4%, Sabinene—0.4%, and other terpenoids.

The Limonene oil (1 part), Carnallite (5 parts) and plant extract (1 part) were mixed with talk powder at a 1:1 w/w ratio to form a powder and 20 mg of the powder was mixed with the inert ingredients, Carbopol 940 and HPMC to form tablets by compression. Tablets without Limonene oil or without Carnallite were prepared and tested on patients with mucosal inflammation and gingivitis. All tablets were very active with the most active is the tablets containing the Limonene and Carnallite. The tablet without active agents had significantly lower activity. Other Citrus essential oils containing 51%, 68%, 76%, and 93% limonene were also used in combination with carnallite salt in a tablet. The activity was correlated to the Limonene content.

Although the effectiveness of said solution is practically instantaneous, the long-term therapeutic effect on the gums is apparent after two weeks, while the periodontal screening index (PSI), continues to increase (indicating an improvement) throughout the duration of applying the above composition.

The first observable phenomenon upon initiating treatment with the above formulation is the disappearance of bleeding from the gums. In addition, during a probing procedure (the measurement of pocket depth), the bleeding effects are significantly lower. At a later stage, the teeth appear to be more rigidly anchored within the gums.

The overall results point to the following attributes:
1. The formula prevents the creation of plaque and dental calculus.
2. The formula cures gum diseases. Gingivitis as well as Periodontitis. Bleeding from the gums stops soon after initiating treatment. The depth of the periodontal pockets is reduced to half within one to two weeks of treatment.
3. The formula quickens the healing processes of inflammatory phenomenon of the oral cavity.
4. The materials have proven to be safe and efficient.
5. In certain situations, we observed the phenomenon of remineralization of the tooth in areas of caries, especially in the cervical area of the tooth.
6. With the curing of the inflammations, the situation of those suffering from an unpleasant odor from the oral cavity (Fetor-Ex-Ore) had improved immensely.

Example 7

Synergistic Antibacterial Compositions

Mixtures of the following herbal components were tested for their antimicrobial activity against the anaerobic and aerobic bacteria, *fusobacterium nucleatum, Streptococus mutans*, and *Actinomyces viscosus* using common MIC determination method. Triptic soy broth, 3.0%, yeast extract 0.1% in water growth media for 48 hours at 37° C. was used for the aerobic bacteria and Triptic soy broth, 3.0%, yeast extract 0.5%, Pepton 1.0%, L-cystein extract, Hemin 0.0001% in water growth media for 48 hours at 37° C. anaerobic was used for the aerobic bacteria The following materials were examined: citron oil, lemon oil, pomella oil, and limonene oil in one group and Cedarwood oil, Berberine, Citronella oil, Juniper berries oil, and grapefruit extract in another group. It was found that any combination between the first group materials and the second group obtained a synergistic anti-microbial effect and a 2 to 10 fold decrease in the MIC.

Combinations of the limonene containing compounds group with one or more of the other group were incorporated in stickers at a concentration of 4 to 10% by weight of the sticker. The stickers, 100 mg, 1×1 mm each, were prepared by tableting of a dry powder of the oils absorbed into talc powder and Carbopol 974, HPMC and Ca-stearate as lubricant (1% w/w). The tablets were tested for their antibacterial activity in vitro in the zone inhibition test and showed a high activity with a release of active agent for at least 10 hours when placed in culture media.

Example 8

Homeopathic Delivery Sticker

Homeopathy is a therapeutic approach based on the concept that disease conditions should be cured by administering drugs which, in healthy people, induce a symptom picture similar to that manifested by the disease one intends to treat. Also typical of homeopathic treatment is that extremely low, and sometimes insimal doses of the homeopathic remedy must be given in order to induce the desired therapeutic effect, whereas high doses of the same drug would actually cause the symptom picture of the disease one is seeking to cure.

Homeopathic preparations are traditionally prepared by means of a method (called "potentization") consisting in a succession of dilutions and succussions of the drug solution; part of the drug (of a vegetable, animal, mineral or synthetic nature) is dissolved (or ground according to the substance) in nine parts of distilled water or alcohol and the resulting mixture is shaken vigorously. Nine parts of this initial solution are taken and diluted with nine parts of water or alcohol and the resulting second diluted solution is again subjected to vigorous succussion. This stage of dilution and succussion can subsequently be repeated several times. Standard potentization levels include the 3× (three times), 6×, 200×, 1000× dilutions, etc. A homeopathic preparation therefore presents itself generally in the form of an extremely dilute solution (aqueous, alcoholic or hydro-alcoholic) of active ingredient.

This type of pharmaceutical formulation severely conditions the mode of administration of homeopathic preparations, limiting it to the oral administration of a number of drops of solution, repeated at one-hourly intervals or, at least, several times a day. Furthermore, to achieve maximum efficacy, the drops of solution must be placed under the tongue and held there for a certain amount of time before being swallowed. For example (see "Applied Homeopathy" by R. Jacobs and M. E. Pinkerson. Homeopathy Press, Santa Monica, Calif., 1983), 10-15 drops of a homeopathic drug for the treatment of neuralgia and sciatica (consisting of Belladonna 6x, Spigelia 6x, Mag.phos. 6x, and Cimifuga 6x) are administered until symptoms are reduced and thereafter the same dose is given 4 times daily until symptoms disappear, holding the solution each time under the tongue for 30 seconds before swallowing it. It will be noted that, though it is advisable to spread the drops of the homeopathic preparation under the patient's tongue, this is still a form of oral and not a form of percutaneous administration, as occurs with sublingual tablets, inasmuch as the solution is actually swallowed after a short space of time.

Sublingual tablets are also used for the administration of homeopathic drugs and present the same drawbacks as already described for solutions.

It is clear that these administration methods, and in particular the need for frequent administrations and for holding the drops of the preparation or the sublingual tablets under the tongue make compliance difficult for any type of patient and particularly difficult for disabled persons, elderly patients and children.

One object of the invention is to provide a new homeopathic carrier for treating local diseases in the oral cavity which when carrying an active ingredient in a homeopathic medicine significantly increases the efficacy of the homeopathic medicine in the desired site. Another object of the invention is to provide a method for preparing such a homeopathic carrier that is in a solid form that provides the exact dose of homeopatic medication for an extended time period in an easy to apply device to the diseased site.

A homeopathic medicine for use in the treatment of bacterial infections is prepared from the following ingredients: 77 drops of a 3x potency solution of a blend of bacterial detoxifying homeopathics, and 1 gallon of the homeopathic carrier solution which contains 1:9 alcohol:water Seventy-seven drops of the 3x potency solution is added to a one gallon bottle. The one gallon bottle was then half filled with the homeopathic carrier solution of example 1 and the bottle is succussed by striking the bottle fifteen times on a leather-bound book. The bottle is then filled with the remainder of the homeopathic carrier solution and the bottle is again succussed by striking the bottle fifteen times on a leather-bound book. The homeopathic medicine is then ready for use. These solutions are incorporated in the bioadhesive solid powder prior to compression mold by adding the proper amount of the daily dose of the homeopathic active drops (3 to 25 drops) to the powder (80 mg of bioadhesive natural gum, i.e. karaya gum) and lyophilization. The dry powder is then compressed into a tablet which is placed onto a oral mucosal lesion.

Active agents that may be included in the formulation are: *Aesculus hippocastanum* extract, *Arnica Montana* extract, *Belladonna, Echinacea angustifolia* extract, *Rhus toxicodendron* extract, *Ruta graveoleus* extract, and Graphites at a typical concentration of 6 mcg/g and *Crotalus horridus* extract, *Heloderma horridum* extract, *Lachesis* extract, *Naja* extract and Mate extract at a typical concentration of 0.08 mcg/g.

The advantages of the homeopathic erodible sticker are: it avoids the need for multiple, repeat administrations in the course of the day at short intervals one from another; mono-administration and, above all, not having to hold the preparation (whether in solution or sublingual tablet form) under the tongue enormously facilitates patient compliance, particularly in the case of disabled persons, elderly patients and children; administration of the drug can be interrupted at any time it may be so desired; the administration is more effective owing to the slow release of the drug.

It will be evident to those skilled in the art that the invention is not limited to the details of the foregoing illustrative embodiments and that the present invention may be embodied in other specific forms without departing from the spirit or essential attributes thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

Example 9

Stickers Releasing Combinations of Agents

Stickers were prepared by mixing fine powders of the active agents and the inert adhesive powders and compress them into tablets that have been used for treating patients. The following drugs were incorporated in different combinations:
anti-microbial—chlorhexidine, povidone-iodine, picoxidine, iodoform, triclosan,
anti-biotics: tetracycline, sulfadiazine, ofloxacin, trimethoprim
anti-fungal: amphotericine B, nystatin, miconazole, triazoles,
anesthetics: lidocaine, benzocaine, tetracaine, kodeine, cokaine,
antiproliphertive/anticollagenase agents
anti-puritic: camphor, phenol, menthol,
anti-viral: acyclovir, acridineamine
anti-ulcerative: acetoxolone, sucralfate, teprenone, omeprazole
Salts: sodium fluoride, Carnallite and its individual salts.

Stickers loaded with a local anesthetic, an antiviral agent, and antimicrobail agent were used.

The following compositions were prepared:

| | | |
|---|---|---|
| a. | benzocaine | 8 mg |
| | amphotericine B | 3 mg |
| | Carbopol 940 | 50 mg |
| | HPMC | 25 mg |
| b. | benzocaine | 6 mg |
| | amphotericine B | 3 mg |
| | ibuprofene | 4 mg |
| | Carbopol 940 | 50 mg |
| | HPMC | 25 mg |
| c. | benzocaine | 8 mg |
| | Chlorhexidine | 3 mg |
| | Carbopol 940 | 50 mg |
| | HPMC | 25 mg |
| d. | benzocaine | 8 mg |
| | triamcinolone | 1 mg |
| | Carbopol 934 | 50 mg |
| | HPMC | 25 mg |
| e. | lidocaine | 2 mg |
| | chlorhexidine | 3 mg |
| | omeprazole | 1 mg |

-continued

| | |
|---|---|
| guanine | 0.5 mg |
| Carbopol 940 | 50 |
| HPMC | 25 |

These compositions were compressed into tablets of 10 mm in diameter. Tablets of 5 mm were prepared by compression 30 mg of the mixtures. Preliminary studies on patielnts indicated an improvement.

What is claimed is:

1. A solid, self-bioadhesive composition for topical application that adheres to oral mucosal tissue comprising:
   (a) a therapeutically effective amount of at least one herbal active agent wherein the herbal active agent is selected from the group consisting of bioactive herbs, herbal extracts, tinctures, essential oils, and mixtures thereof, and
   (b) a pharmaceutically acceptable solid bioadhesive carrier, comprising one or more mucoadhesive synthetic crosslinked polycarboxylic acid polymers, in an amount from about 40 to 99 percent based on the weight of the whole composition in a form suitable for administration and adhesion to the oral mucosa.

2. The solid composition of claim 1 wherein the composition is in the form of a disc of 2 to 15 mm diameter and 0.4 to 2.3 mm thick that adheres to the oral mucosal tissue for at least 30 minutes.

3. The solid composition of claim 1 where the composition is in the form of a disc 5 to 11 mm in diameter and 1 to 2 mm thick with tissues adherence of at least 1 hour.

4. The composition of claim 1 wherein the herbal active agent is selected from the group consisting of anti-inflammatory, analgesic, antiaching, anesthetic, antimicrobial, antifungal, antiseptic, antiviral, antibiotic, antiparasite agents, and combinations thereof.

5. The composition of claim 1 wherein the herbal agent is selected from the group consisting of *Echinacea, Salvia officinalis, Hypericum*, Myrrh, *Camphoria, Uncaria*, menthol, *Plantago, Baptisia, Calendula, Phytolacca*, Catechu black, Coneflower, *Krameria*, Tsuga, grape fruit seed extract, *Rosmarinus, Styrax, Crataegus, Glycerrhiza, Angelica, Kramerica, Matricaria*, Mallow, Propolis, Sage, berberine from *hydrastis canadensis* L., plant family Berberidaceae, gentian from the gentianaceae family of plants for the treatment of fungal infections, monoterpenes of three unsaturations, *Taraxacum* extract, *Lonicera* flower extract, *Scutellaria* root extract, *Gardenia* fruit extract, *Pulsatilla* root extract, *Pueraria* root extract, *Radix gentianae* Longdancao antifungal agent, and combinations thereof.

6. The composition of claim 1, wherein the herbal active agent is an essential oil selected from the group consisting of citronella oil, lemon oil, citron oil, pomelo peel oil, cedarwood oil, juniper berries oil, lemon basil oil, *Rosmarinus officinalis* oil, cinnamon oil, cajeput oil, *eucalyptus* oil, fennel oil, *geranium* oil, girofle oil, lavendar oil, clove oil, spearmint oil, myrtle oil, oregano oil, pine oil, rosemary oil, sarriette oil, thyme oil, tea-tree oil, and combinations thereof.

7. The composition of claim 6, wherein the herbal active agent is an essential oil selected from the group consisting of cinnamon oil, tea-tree oil, citronella oil, and combinations thereof.

8. The composition of claim 5, wherein the herbal active agent comprises at least one monoterpene with three unsaturations.

9. The composition of claim 1, wherein the herbal active agent is an essential oil and the essential oil is a natural or synthetic mixture consisting of limonene and at least one myrcene, a-pinene, b-pinene, and sabinene characterized in that at least 60% by weight of the mixture is limonene.

10. The composition of claim 8, wherein the monoterpene with three unsaturations is a citrus oil selected from the group consisting of lemon oil, pomelo oil, citron oil, and combinations thereof.

11. The composition of claim 1, further comprising a salt selected from the group consisting of $MgBr_2$, NaCl, KCl and mixtures thereof.

12. The composition of claim 1 further comprising Carnallite or a salt of Carnallite.

13. The composition of claim 1, further comprising a non-herbal active agent.

14. The composition of claim 13, wherein the non-herbal active agent is selected from the group consisting of at least one base or acid-addition salt of procaine, lidocaine, prilocalne, mepivacaine, dyclonine, dibucaine, benzocaine, chloroprocaine, tetracaine, bupivacaine, and etidocaine.

15. The composition of claim 13, wherein the non-herbal active agent is selected from the group consisting of at least one base or acid-addition salt of dexamethasone, triamcinolone, hydrocortisone, amphotericine B, nystatin, itraconazole, chlorhexidine, quaternary ammonium salts, parabens, and dextranase enzymes.

16. The composition of claim 1, wherein the active agent consists of a mixture of natural or synthetic monoterpenes with three unsaturations selected from the group consisting of limonene, myrcene, pinenes, sabinene, and terpinene.

17. The composition of claim 13 comprising a citron oil and Carnallite salt at a ratio between 1:10 and 1:1.

18. The composition of claim 13 comprising a citron oil and Carnallite salt at a ratio between 1:10 and 1:1 and a local anesthetic selected from the group consisting of lidocaine, benzocaine, and bupivecaine.

19. The composition of claim 1 wherein the polymer further comprises a polymer or copolymer selected from the group consisting of hydroxypropyl cellulose, hydroxypropyl methylcellulose, hydroxyethylcellulose, carboxymethyl cellulose, dextran, arabinogalactan, pullulan, guar-gum, hyaluronic acid, pectins, starch derivatives, acrylic acid polymers, polymer of acrylic acid esters, polymers of vinyl alcohols, alkoxy polymers, polyethylene oxide polymers, polyethers and combinations thereof.

20. The composition of claim 1 further comprising an excipient selected from the group consisting of fillers, tableting excipients, lubricants, enhancers, flavors, taste-masking agents, pH controlling compounds, dyes, stabilizers, enzyme inhibitors, and mixtures thereof.

21. The composition of claim 20 wherein the enhancers are selected from the group consisting of bile acids and limonene.

22. The composition of claim 1 wherein the solid bioadhesive carrier is selected from polyacrylic acid polymers crosslinked with a polymer selected from the group consisting of polyalkenyl polyether, carboxymethylceullose, hydroxymethylcellulose, and mixtures thereof.

23. The composition of claim 1, wherein the composition has a surface area ranging from about 0.4 to about 3 $cm^2$.

24. The composition of claim 22, wherein the bioadhesive carrier comprises a polyacrylic acid polymer crosslinked with a polyalkenyl ether.

25. The composition of claim 24, wherein the polyalkenyl ether is allyl pentaerythritol.

26. The composition of claim 25, wherein the bioadhesive carrier further comprises a cellulosic polymer.

27. The composition of claim 26, wherein the cellulosic polymer is hydroxy propyl cellulose.

* * * * *

UNITED STATES PATENT AND TRADEMARK OFFICE
CERTIFICATE OF CORRECTION

PATENT NO. : 7,943,169 B2  
APPLICATION NO. : 10/083413  
DATED : May 17, 2011  
INVENTOR(S) : Avraham J. Domb and Joseph Simcha Wolnerman Page 1 of 1

It is certified that error appears in the above-identified patent and that said Letters Patent is hereby corrected as shown below:

Claim 14, column 26, lines 15-16, replace "prilocalne" with --prilocaine--.

Claim 22, column 26, line 52, replace "carboxymethylceullose" with --carboxymethylcellulose--.

Signed and Sealed this  
Twenty-second Day of May, 2012

David J. Kappos  
*Director of the United States Patent and Trademark Office*